United States Patent
Nishigaki et al.

(10) Patent No.: US 10,379,440 B2
(45) Date of Patent: Aug. 13, 2019

(54) PATTERN FORMING METHOD, SEMICONDUCTOR DEVICE, AND MANUFACTURING METHOD THEREOF

(71) Applicant: KABUSHIKI KAISHA TOSHIBA, Minato-ku, Tokyo (JP)

(72) Inventors: Michihiko Nishigaki, Kawasaki Kanagawa (JP); Yutaka Onozuka, Yokohama Kanagawa (JP); Shouhei Kousai, Yokohama Kanagawa (JP); Yosuke Akimoto, Yokohama Kanagawa (JP); Miyu Nagai, Yokohama Kanagawa (JP); Kaita Imai, Tokyo (JP)

(73) Assignee: KABUSHIKI KASHIA TOSHIBA, Tokyo (JP)

( * ) Notice: Subject to any disclaimer, the term of this patent is extended or adjusted under 35 U.S.C. 154(b) by 0 days.

(21) Appl. No.: 15/694,597

(22) Filed: Sep. 1, 2017

(65) Prior Publication Data
US 2018/0217500 A1    Aug. 2, 2018

(30) Foreign Application Priority Data
Jan. 27, 2017    (JP) .................................. 2017-013188

(51) Int. Cl.
*B01L 3/00*    (2006.01)
*G03F 7/11*    (2006.01)
(Continued)

(52) U.S. Cl.
CPC .......... *G03F 7/0757* (2013.01); *B01L 3/5085* (2013.01); *G03F 7/11* (2013.01);
(Continued)

(58) Field of Classification Search
CPC ..... H01L 51/56; H01L 33/62; H01L 51/0072; H01L 51/5092; H01L 51/5016
(Continued)

(56) References Cited

U.S. PATENT DOCUMENTS

| 5,962,581 A * | 10/1999 | Hayase .................. C08K 3/36 427/387 |
| 6,448,346 B1 * | 9/2002 | Noguchi .................. B41J 2/16 346/140.1 |

(Continued)

FOREIGN PATENT DOCUMENTS

| JP | 2011210972 A | 10/2011 |
| JP | 2014139009 A | 7/2014 |

(Continued)

OTHER PUBLICATIONS

J. Garra et al., "Dry etching of polydimethylsiloxane for microfluidic systems," Journal of Vacuum Science & Technology A: Vacuum, Surfaces, and Films (vol. 20, No. 3), May 2002, pp. 975-982.

(Continued)

*Primary Examiner* — Andy Huynh
(74) *Attorney, Agent, or Firm* — Holtz, Holtz & Volek PC

(57) ABSTRACT

According to one embodiment, a pattern forming method includes forming a resist pattern on a substrate, forming a first silicone resin layer so as to bury the resist pattern on the substrate, pressing a film on the surface of the first silicone resin layer to adhere the film thereto, curing the first silicone resin layer after the adhesion of the film, peeling the film from the first silicone resin layer before or after the curing of the first silicone resin layer, and removing the resist pattern after the peeling of the film.

5 Claims, 8 Drawing Sheets

(51) Int. Cl.
*G03F 7/20* (2006.01)
*G03F 7/32* (2006.01)
*G01N 21/05* (2006.01)
*G01N 21/64* (2006.01)
*G03F 7/075* (2006.01)
*H01L 21/027* (2006.01)

(52) U.S. Cl.
CPC ............ *G03F 7/2004* (2013.01); *G03F 7/325* (2013.01); *H01L 21/0274* (2013.01); *B01L 2200/12* (2013.01); *B01L 2300/0636* (2013.01); *B01L 2300/0663* (2013.01); *B01L 2300/0829* (2013.01); *B01L 2300/0851* (2013.01); *G01N 21/6486* (2013.01); *G01N 2021/054* (2013.01); *G01N 2021/6482* (2013.01)

(58) Field of Classification Search
USPC ........................................................ 257/414
See application file for complete search history.

(56) References Cited

U.S. PATENT DOCUMENTS 9,263,649 B2 2/2016 Koike et al.
2013/0273741 A1* 10/2013 Yamamoto ........... C09D 183/04
                                                            438/694
2014/0332098 A1 11/2014 Juncker et al.
2015/0158268 A1 6/2015 Koike et al.

FOREIGN PATENT DOCUMENTS

JP         2014525569 A    9/2014
WO        2012176728 A1   12/2012

OTHER PUBLICATIONS

Kee Suk Ryu et al., "A Method for Precision Patterning of Silicone Elastomer and Its Applications," Journal of Microelectromechanical Systems (vol. 13, No. 4), Aug. 9, 2004, pp. 568-575.

\* cited by examiner

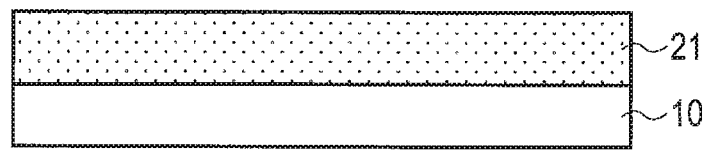
F I G. 2A
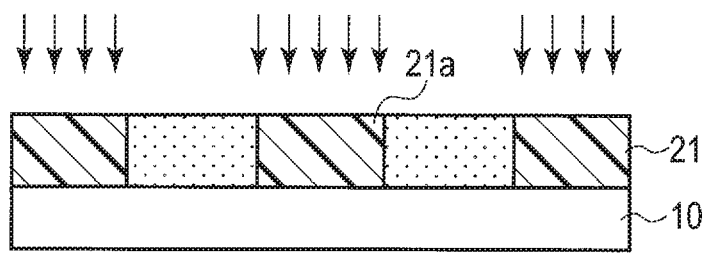
F I G. 2B
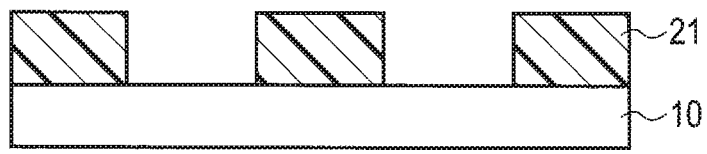
F I G. 2C

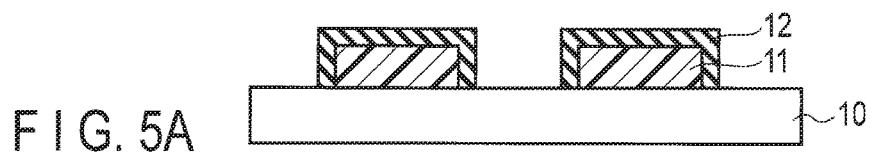
F I G. 5A
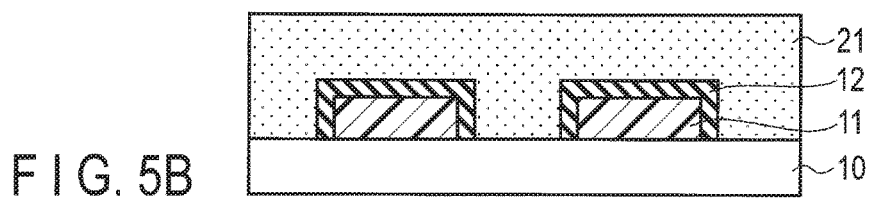
F I G. 5B
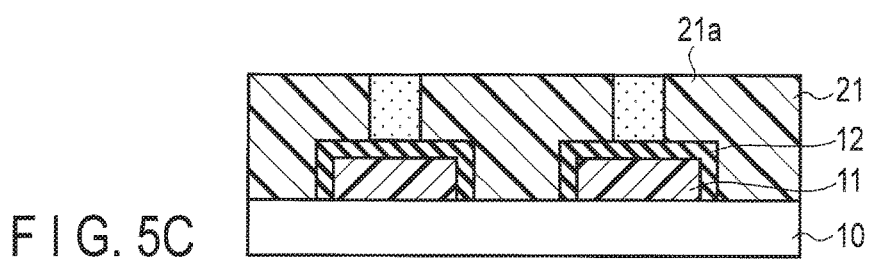
F I G. 5C
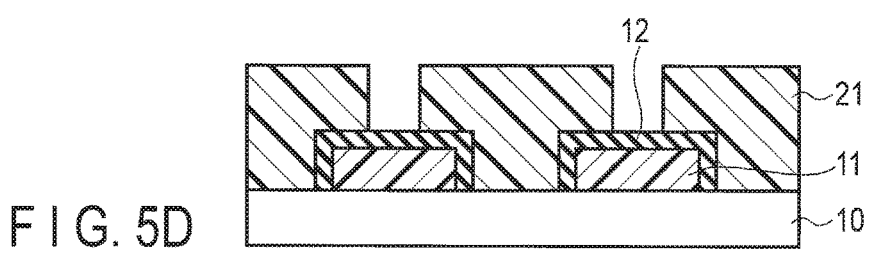
F I G. 5D
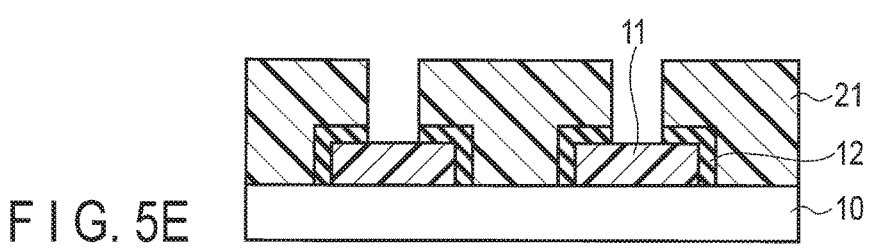
F I G. 5E
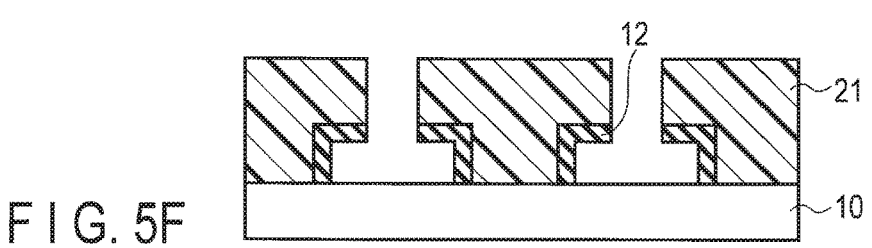
F I G. 5F

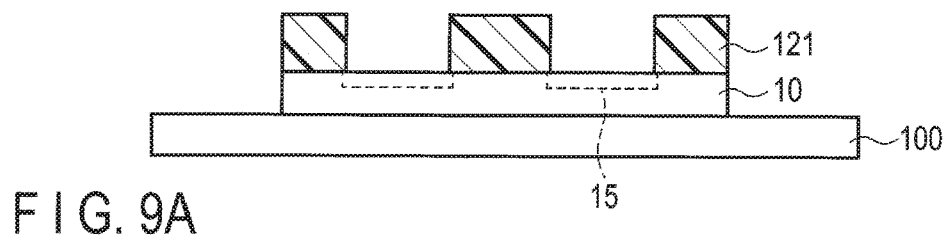
F I G. 9A
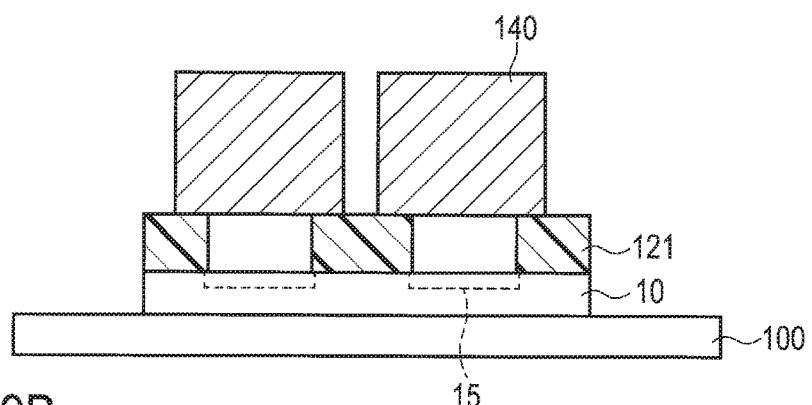
F I G. 9B
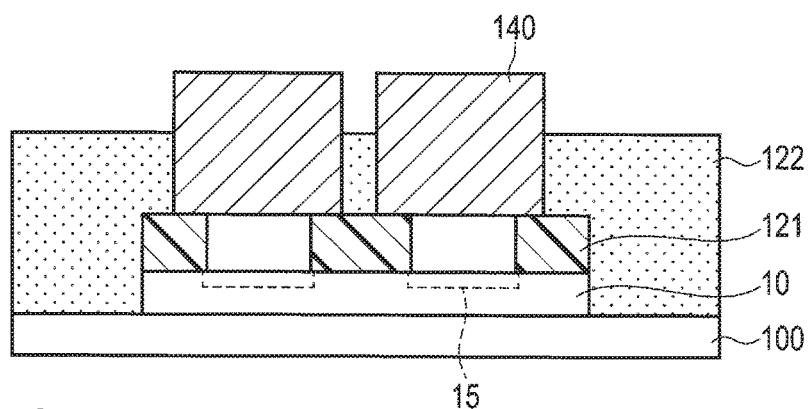
F I G. 9C
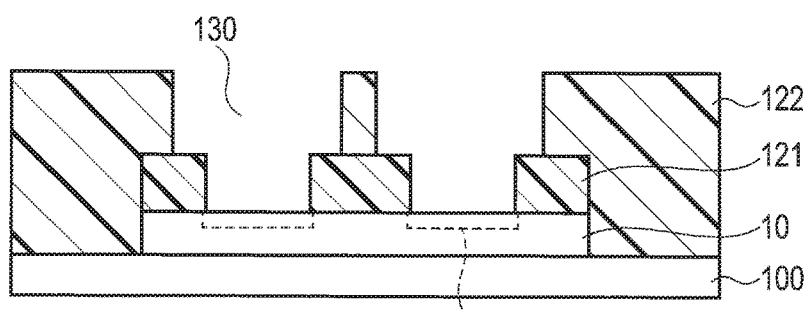
F I G. 9D

# PATTERN FORMING METHOD, SEMICONDUCTOR DEVICE, AND MANUFACTURING METHOD THEREOF

CROSS-REFERENCE TO RELATED APPLICATIONS

This application is based upon and claims the benefit of priority from Japanese Patent Application No. 2017-013188, filed Jan. 27, 2017, the entire contents of which are incorporated herein by reference.

FIELD

Embodiments described herein relate generally to a pattern forming method using a silicone resin, a semiconductor device using a silicone resin, and a manufacturing method thereof.

BACKGROUND

In recent years, various types of biosensors are developed for inspection of cells, sample liquids, and the like. In some cases, a silicone resin such as poly-dimethyl-siloxane (PDMS) is used in a bank structure and a channel structure in the biosensors.

However, because of its chemically stable property, the silicone resin is difficult to treat in a conventional semiconductor process. Thus, forming the bank structure, channel structure, and the like with a silicone resin into a suitable pattern is difficult.

BRIEF DESCRIPTION OF THE DRAWING

FIGS. 2A to 2C are cross-sectional views showing processes of a pattern forming method of a second embodiment.

FIGS. 5A to 5F are cross-sectional views showing processes of a pattern forming method of a fifth embodiment.

FIGS. 9A to 9D are cross-sectional views showing processes of a manufacturing method of a semiconductor device of the seventh embodiment.

DETAILED DESCRIPTION

In general, according to an embodiment, a pattern forming method comprises: forming a resist pattern on a substrate; forming a first silicone resin layer so as to bury the resist pattern on the substrate; pressing a film on the surface of the first silicone resin layer to adhere the film thereto; curing the first silicone resin layer after the adhesion of the film; peeling the film from the first silicone resin layer before or after the curing of the first silicone resin layer; and removing the resist pattern after the peeling of the film.

Hereinafter, details of embodiments will be explained with reference to the accompanying drawings.

First Embodiment

FIGS. 1A to 1E are cross-sectional views showing a pattern forming method of a first embodiment and showing pattern forming processes. In this embodiment, a convex bank structure is formed on a substance to surround a sensor part (which is not shown) formed on the substrate, for example. Note that the present embodiment is applied to a biosensor configured to inspect cells, sample liquids, and the like, and the bank structure is a component of such a biosensor.

Figure 1A:
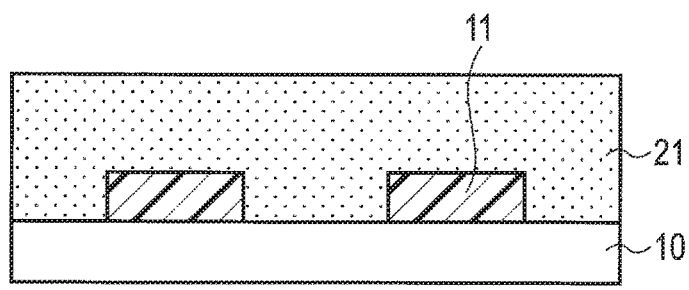
FIGS. 1A to 1E are cross-sectional views showing processes of a pattern forming method of a first embodiment.

Initially, as shown in FIG. 1A, a convex resist pattern 11 is formed on a semiconductor substrate 10 formed of Si or the like. Specifically, the resist pattern 11 is formed by applying a photoresist on the semiconductor substrate 10, exposing into a desired pattern, and then developing the photoresist. Then, an ultraviolet-cured silicone resin such as PDMS is applied on the semiconductor substrate 10 to cover the resist pattern 11. Through the above steps, a silicone resin layer 21 is formed.

Figure 1B:
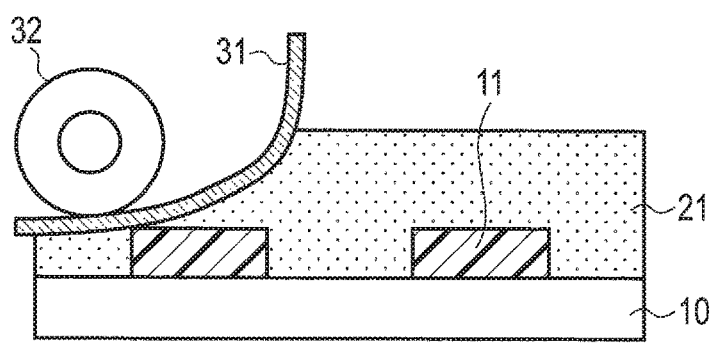

Then, as shown in FIG. 1B, a transparent laminate film 31 is, in a vacuum, pressed and adhered to the surface of the silicon resin layer 21. Specifically, the film 31 is pressed against the surface of the silicone resin layer 21 with a constant pressure force using a roller 32. Then, the roller 32 is rotated and moved in parallel to the film 31 to adhere the film 31 on the surface of the silicone resin layer 21. Therefore, the silicone resin layer 21 and the upper surface of the resist pattern 11 become substantially the same height and the thickness thereof becomes even.

Note that, a pressure used for adhesion of the film 31 is, preferably, 10 torr or less. Furthermore, the roller 32 used in the adhesion of the film 31 is pressed at 1 kgf/cm$^2$ or more.

Figure 1C:
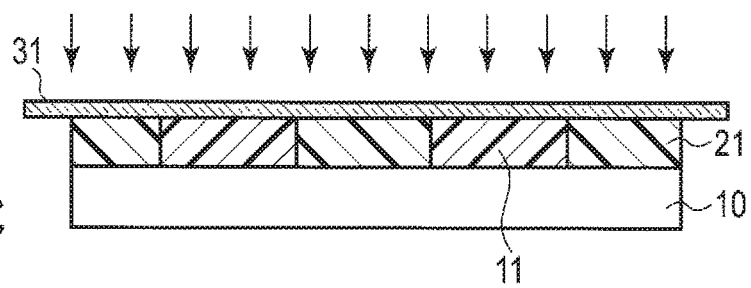

Then, as shown in FIG. 1C, ultraviolet is irradiated onto the silicone resin layer 21 through the film 31 to cure the silicone resin layer 21. Here, the film 31 passes ultraviolet of wavelength of 436 nm or less. Furthermore, if the film 31 does not pass ultraviolet, ultraviolet may be irradiated after peeling the film 31.

Note that, if a thermal-cured silicone resin is used, infrared may be irradiated thereon instead of ultraviolet or the resin layer may be cured by heating with a heater.

Figure 1D:
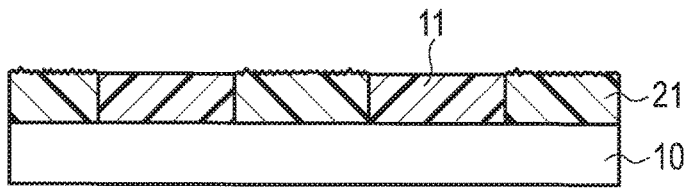
Figure 1E:
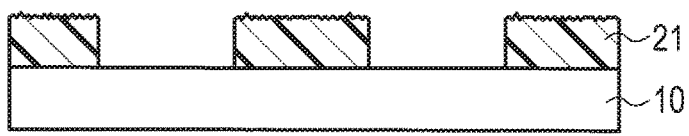

Then, as shown in FIG. 1D, the film 31 is peeled off from the silicone resin layer 21. Then, a residue of the silicone resin layer 21 on the resist pattern 11 is removed by dry etching or grinding. The residue removed here is an extremely small amount, and almost no damage is applied to the silicone resin layer 21 by the residue removal.

Then, as shown in FIG. 1F, the resist pattern 11 is removed using an etchant having selectivity with respect to the silicone resin layer 21 such as acetone or a resist remover. Thus, a pattern of the silicone resin layer 21 is formed on the semiconductor substrate 10.

In the present embodiment, since the film 31 is adhered to the silicone resin layer 21, the silicone resin layer 21 can be formed flat. Furthermore, since the resist pattern 11 can be removed after the flattening of the silicone resin layer 21, etching of the thick film of the silicone resin layer 21 is not required. This achieves an effect of preventing deterioration of the silicone resin layer 21 by etching. Furthermore, since the press of the film 31 is performed in a vacuum, occurrence of a void can be suppressed.

For example, if a convex silicone resin layer is formed by molding, the silicone resin layer is required to be adhered to a different substrate. However, in such a case, a contacting surface to the substrate is limited, and a contacting force is weakened, for example. Furthermore, in dry etching of a thick film of the silicone resin layer, a deteriorated layer is formed on the surface of the silicone resin layer, and adhesion to a different substrate may be difficult to perform. Furthermore, in grinding of the thick film of the silicone resin layer, a surface roughness and a side surface residue may occur.

In contrast, in the present embodiment, through very simple processes of adhesion of the film 31 and removal of the resist pattern 11, a convex pattern of a silicone resin with a flat surface having less surface roughness and less side surface residue can be suitably formed on the substrate. That is, a bank structure of good pattern can be achieved using a silicone resin.

Second Embodiment

FIGS. 2A to 2C are cross-sectional views showing processes of a pattern forming method of a second embodiment. Note that elements which are same with those in FIGS. 1A to 1F are referred to by the same reference numbers and their detailed description will be omitted. In this embodiment, a bank structure is formed on a substrate.

Initially, as shown in FIG. 2A, an ultraviolet-cured silicone resin is applied on a semiconductor substrate 10, and a silicone resin layer 21 is formed. The silicone resin layer 21 is cured by irradiation of ultraviolet. Or, an ultraviolet-activated thermal-cured silicone resin which is activated by the irradiation of ultraviolet and cured by heating may be used.

Then, as shown in FIG. 2B, ultraviolet is selectively irradiated on the part where the silicone resin layer 21 is remained in a convex shape and the irradiated part is cured. In the figure, an area denoted by 21a is a cured part of the silicone resin layer 21. Note that, if the silicone resin layer 21 is ultraviolet-activated and thermal-cured, ultraviolet is irradiated and then, the entire resin layer is heated in, for example, a nitrogen atmosphere oven.

Then, as shown in FIG. 2C, the uncured part of the silicone resin layer 21 is removed by a developer.

A developer used here dissolves a silicone resin. For example, the developer contains at least one of diisopropylamine, trimethylamine, pentane, perfluorotributylamine, perfluorodecalin, xylene, ether, hexane, trichloroethylene, normal heptane, cyclohexane, dimethoxyethane, toluene, ethyl acetate, and ethyl methyl ketone, as a solvent.

In the second embodiment, a pattern can be formed through very simple processes of selective ultraviolet irradiation and development after forming the silicone resin layer 21. Thus, as in the first embodiment, a good pattern of the silicone resin layer 21 can be manufactured on the semiconductor substrate 10.

Third Embodiment

FIGS. 3A to 3D are cross-sectional views showing processes of a pattern forming method of a third embodiment. Note that elements which are same with those in FIGS. 1A to 1E are referred to by the same reference numbers and their detailed description will be omitted. In this embodiment, a bank structure is formed on a substrate.

Figure 3A:
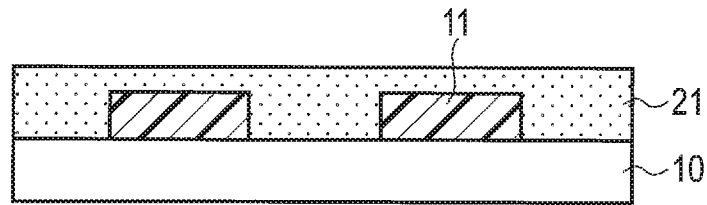
FIGS. 3A to 3D are cross-sectional views showing processes of a pattern forming method of a third embodiment.

Initially, as shown in FIG. 3A, as in the first embodiment, a convex resist pattern 11 is formed on a semiconductor substrate 10 formed of Si or the like. Then, an ultraviolet-cured silicone resin such as PDMS is applied on the semi-conductor substrate 10 to cover the resist pattern 11, and a silicone resin layer 21 is formed. At that time, the thickness of the silicone resin layer 21 is slightly greater than the thickness of the resist pattern 11.

Figure 3B:
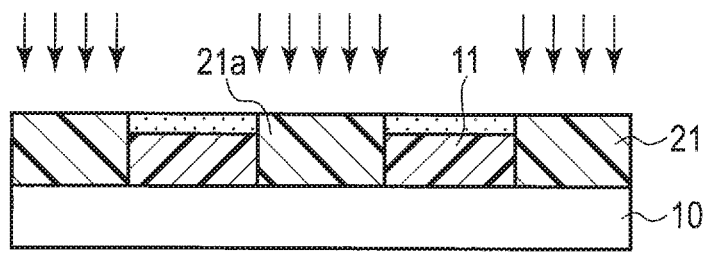

Then, as shown in FIG. 3B, ultraviolet is irradiated on the silicone resin layer 21 except for a region of the resist pattern 11 to cure the irradiated part. In the figure, an area denoted by 21a is the cured part of the silicone resin layer 21.

Figure 3C:
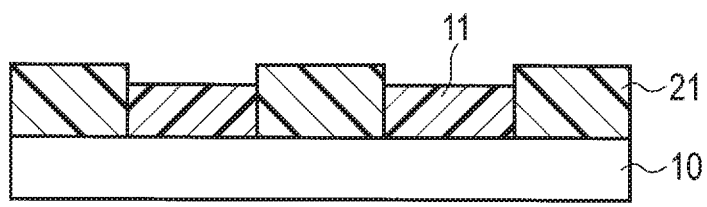

Then, as shown in FIG. 3C, an uncured silicone resin layer 21 is removed by a developer explained in the section of the second embodiment. At that time, since the thickness of the uncured silicone resin layer 21 removed is small, and thus, damage to the cured part of the silicone resin layer 21 by the developer is ignorable.

Figure 3D:
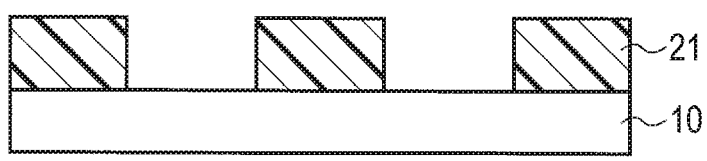

Then, as shown in FIG. 3D, the resist pattern 11 exposed by the removal of the silicone resin layer 21 is removed by an etchant having selectivity with respect to the silicone resin layer 21.

In the present embodiment, as in the second embodiment, a convex pattern can be formed through very simple processes of selective ultraviolet irradiation and development to the silicone resin layer 21. Furthermore, as compared to the second embodiment, the thickness of the silicone resin layer 21 to be removed is smaller. Thus, damage to the part of the silicone resin layer 21 to be maintained as a convex pattern can be decreased.

Note that, if the thickness of the silicone resin layer 21 is significantly greater than the thickness of the resist pattern 11, as in the first embodiment, a transparent laminate film 31 is pressed and adhered to the surface of the silicone resin layer 21, and in this state, selective ultraviolet irradiation and curing are performed to the silicone resin layer 21. Then, a residue on the resist pattern 11 is removed by a developer after peeling the transparent laminate film 31.

Fourth Embodiment

FIGS. 4A to 4D are cross-sectional views showing processes of a pattern forming method of a fourth embodiment. Note that elements which are same with those in FIGS. 1A to 1E are referred to by the same reference numbers and their detailed description will be omitted. In this embodiment, a channel to feed a sample liquid or the like is formed on a substrate.

Figure 4A:
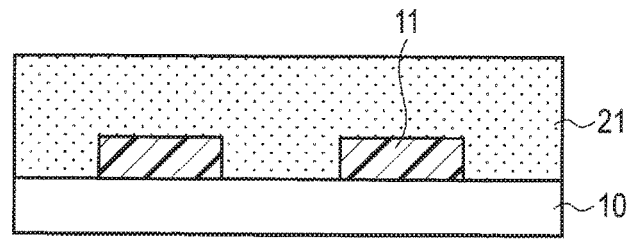
FIGS. 4A to 4D are cross-sectional views showing processes of a pattern forming method of a fourth embodiment.

Initially, as shown in FIG. 4A, a resist pattern 11 is formed in a pattern of a channel on a semiconductor substrate 10 formed of Si or the like. Specifically, a channel pattern is formed by photolithography after applying a resist on the semiconductor substrate 10. Then, an ultraviolet-cured silicone resin such as PDMS is applied on the semiconductor substrate 10 to cover the resist pattern 11. Through the above steps, a silicone resin layer 21 is formed.

Figure 4B:
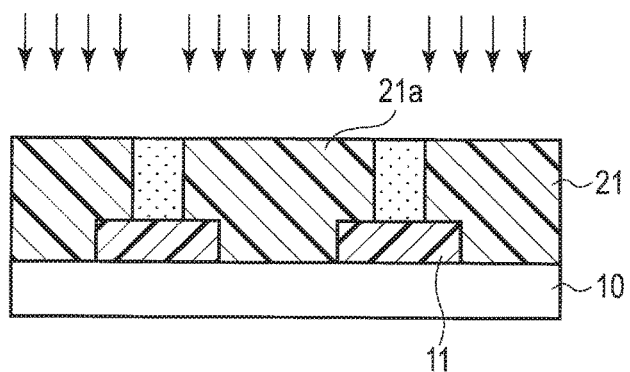

Then, as shown in FIG. 4B, ultraviolet is partly irradiated to avoid the resist pattern 11. Specifically, ultraviolet is irradiated on the silicone resin layer 21 except for the part to be an opening connected to the channel, and the silicone resin layer 21 is cured. In the figure, an area denoted by 21a is a cured part of the silicone resin layer 21.

Figure 4C:
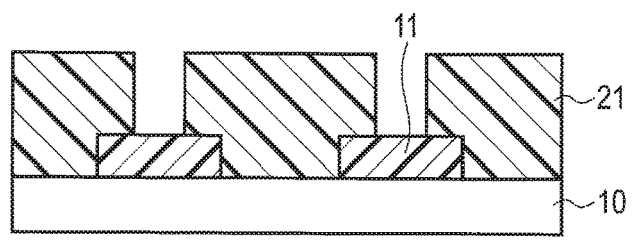

Then, as shown in FIG. 4C, an uncured part of the silicone resin layer 21 is removed by a developer which is explained in the section of the second embodiment.

Figure 4D:
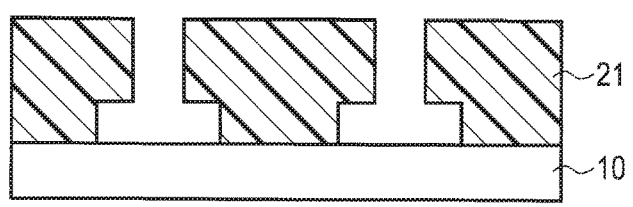

Then, as shown in FIG. 4D, the resist pattern 11 exposed by the removal of the silicone resin layer 21 is removed by an etchant having selectivity with respect to the silicone resin layer 21. Therefore, a channel which has side walls and upper wall formed of the silicone resin layer 21 is manufactured.

As can be understood from the above, in the present embodiment, a channel formed of the silicone resin layer 21 can be formed on the semiconductor substrate 10. In that case, the channel is not formed by direct patterning of the silicone resin layer 21 but is formed by removal of the resist pattern 11. Thus, a channel of good pattern can be manufactured.

Here, a silicone resin is, for example, almost harmless to cells, less autofluorescence or less luminous, and highly transparent. In the present embodiment, a sample liquid used for the bio material inspection touches the silicone resin inside the channel except for the semiconductor substrate 10, and thus, the channel is suitable for sample liquid feeding.

Fifth Embodiment

FIGS. 5A to 5F are cross-sectional views showing processes of a pattern forming method of a fifth embodiment. Note that elements which are same with those in FIGS. 4A to 4D are referred to by the same reference numbers and their detailed description will be omitted.

This embodiment is a variation of the fourth embodiment and includes a process of forming a protection film. In this respect, the present embodiment is different from the fourth embodiment.

Initially, as shown in FIG. 5A, a resist pattern 11 to be a channel is formed on a semiconductor substrate 10 formed of Si or the like. Then, a protection film 12 is formed to cover the resist pattern 11. As the protection film 12, an oxide film such as $SiO_2$, a nitride film such as SiN, or a paraxylene polymer (polyparaxylene resin) film may be used.

An oxide film or a nitride film can be formed through sputtering or plasma CVD. A polyparaxylene resin film can be coated by setting a sample in vaporized polyparacylene resin. Here, the oxide film, nitride film, and polyparaxylene resin used as the protection film 12 are effective since they can be formed in a temperature which is below the maximum heat resistance of a photoresist (from a room temperature to approximately 150° C.). Furthermore, they are effective since they can achieve high adherence to the silicone resin formed thereon.

Then, as shown in FIG. 5B, an ultraviolet-cured silicone resin such as PDMS is applied on the semiconductor substrate 10 to cover the resist pattern 11 and the protection film 12. Through the above steps, a silicone resin layer 21 is formed.

Then, as shown in FIG. 5C, ultraviolet is partly irradiated to avoid the resist pattern 11. Specifically, ultraviolet is irradiated on the silicone resin layer 21 except for the part to be an opening connected to the channel, and the silicone resin layer 21 is cured. In the figure, an area denoted by 21a is a cured part of the silicone resin layer 21.

Then, as shown in FIG. 5D, an uncured part of the silicone resin layer 21 is removed by a developer explained in the section of the second embodiment.

Then, as shown in FIG. 5E, the protection film 12 selectively etched using the silicone resin layer 21 as a mask.

Then, as shown in FIG. 5F, the resist pattern 11 exposed by removal of the silicone resin layer 21 and the protection film 12 is removed by an etchant having selectivity with respect to the silicone resin layer 21. Therefore, a channel which has side walls and upper wall coated with the protection film 12 is manufactured.

As can be understood from the above, in the present embodiment, a channel which is formed of the silicone resin layer 21 and which has side walls and upper wall coated with the protection film 12 can be formed on the semiconductor substrate 10. In that case, the channel is not formed by direct patterning of the silicone resin layer 21 but is formed by removal of the resist pattern 11. Thus, a channel of good pattern can be manufactured.

Furthermore, in the present embodiment, in addition to the structure of the fourth embodiment, the protection film 12 is provided, and the following advantage is obtained.

If the channel is formed in the silicone resin layer 21, it is effective to increase the wettability of the side surfaces and upper surface of the channel to make the flow of the sample liquid in the channel smooth and suppress the generation of bubbles. As in the present embodiment, if the protection film 12 is formed of a hydrophilic material such as an oxide film, the wettability of the side surfaces and upper surface of the channel can further be improved as compared to a case where a silicone resin as a channel is exposed. Furthermore, if the protection film 12 is formed of a hydrophobic material such as a nitride film or a polyparaxylene resin, the hydrophilicity of surfaces in the channel can be increased by oxygen plasma processing.

Note that an oxide film passes moisture, and if this should be avoided, a nitride film or a polyparaxylene resin film may be layered on the oxide film. In that case, although the side surfaces and upper surface are hydrophilic, moisture does not pass the film.

As a desired layered structure for the protection film 12, for example, an oxide film/nitride film (lower side/upper side), oxide film/polyparaxylene resin film, or polyparaxylene resin film/oxide film can be adopted. First two structures can improve the wettability by the oxide film and can suppress permeability by the nitride film or the polyparaxylene resin film. The last one can suppress the permeability by the polyparaxylene resin film and the oxide film can improve adherence to PDMS.

Sixth Embodiment

FIGS. 6A to 6E are cross-sectional views showing processes of a pattern forming method of a sixth embodiment. Note that elements which are same with those in FIGS. 1A to 1E are referred to by the same reference numbers and their detailed description will be omitted. In this embodiment, a channel is formed.

Figure 6A:
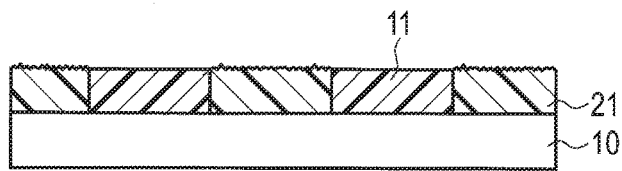
FIGS. 6A to 6E are cross-sectional views showing processes of a pattern forming method of a sixth embodiment.

Initially, as shown in FIG. 6A, a resist pattern 11 to be a channel is formed on a semiconductor substrate 10 formed of Si or the like and sides of the resist pattern 11 is embedded by the first silicone resin layer 21. Specifically, similar processes as shown in FIGS. 1A to 1D of the first embodiment are performed.

Figure 6B:
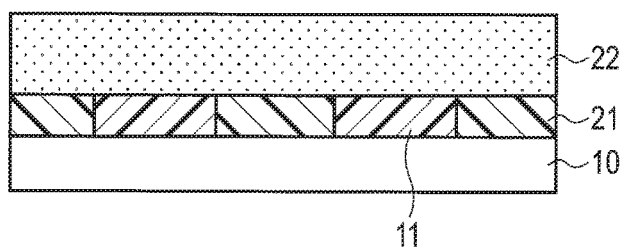

Then, as shown in FIG. 6B, a second silicone resin is applied on the resist pattern 11 and the first silicone resin layer 21 to form a second silicone resin layer 22. The second silicone resin layer 22 is, as with the first silicone resin layer 21, ultraviolet-cured.

Figure 6C:
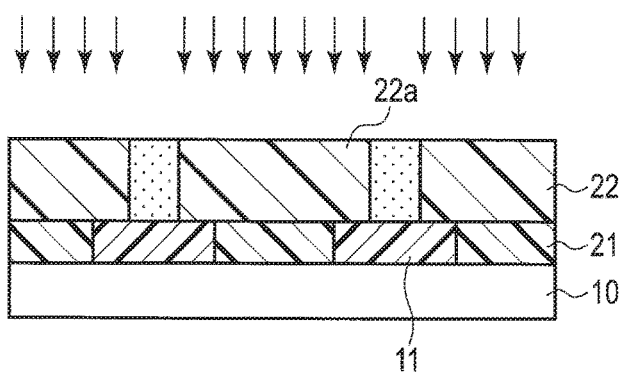

Then, as shown in FIG. 6C, ultraviolet is partly irradiated to avoid the resist pattern 11. Specifically, ultraviolet is irradiated on the silicone resin layer 22 except for the part to be an opening connected to the channel, and the silicone resin layer 22 cured. In the figure, an area denoted by 22a is a cured part of the silicone resin layer 22.

Figure 6D:
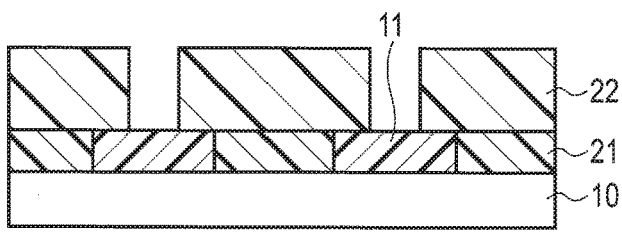

Then, as shown in FIG. 6D, an uncured part of the silicone resin layer 22 is removed by a developer explained in the section of the second embodiment.

Figure 6E:
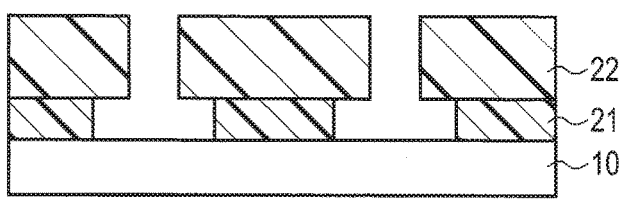

Then, as shown in FIG. 6E, the resist pattern 11 exposed by the removal of the silicone resin layer 22 is removed by an etchant having selectivity with respect to the silicone resin layer 21. Therefore, a channel which has side walls formed of the silicone resin layer 21 and upper wall formed of the silicone resin layer 22 is manufactured.

As can be understood from the above, in the present embodiment, a channel which is formed of the silicone resin layers 21 and 22 can be formed on the semiconductor substrate 10. In that case, the channel is not formed by direct patterning of the silicone resin layer 22 but is formed by removal of the resist pattern 11. Thus, a channel of good pattern can be manufactured.

Seventh Embodiment

Figure 7:
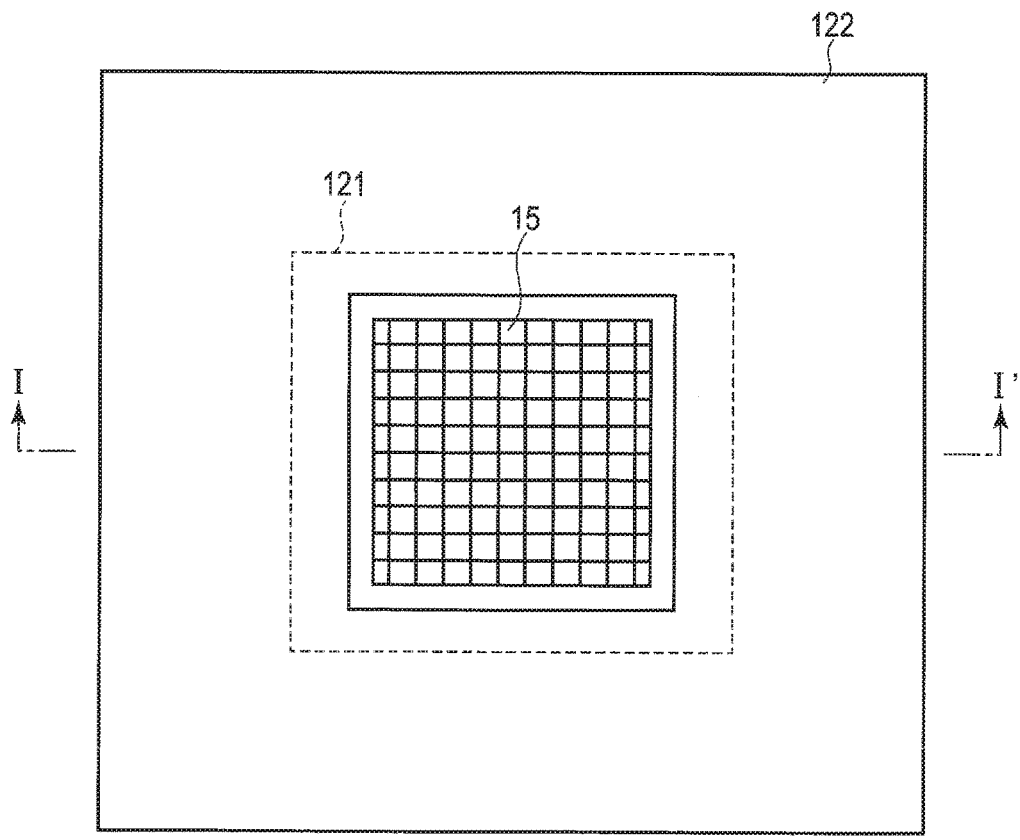
FIG. 7 is a plan view showing a schematic structure of a semiconductor device of a seventh embodiment.
Figure 8:
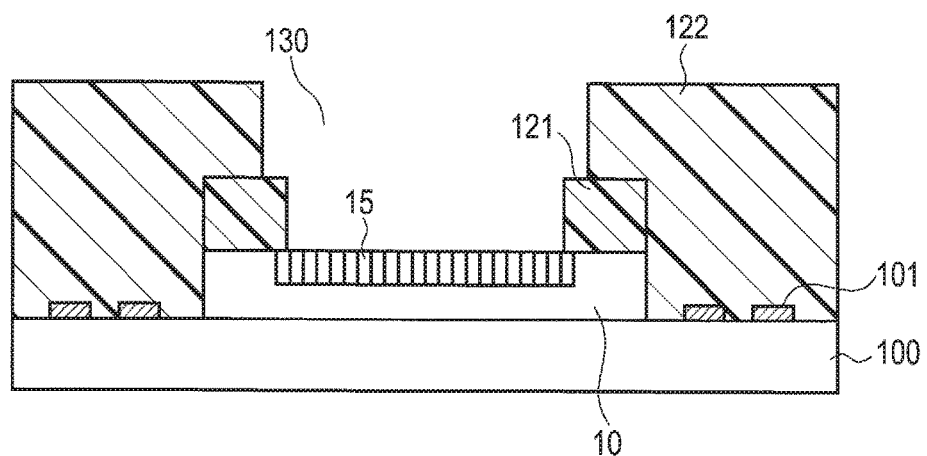
FIG. 8 is a cross-sectional view of the semiconductor device taken along line I-I' of FIG. 7.

FIGS. 7 and 8 show a schematic structure of a semiconductor device of a seventh embodiment. FIG. 7 is a plan view and FIG. 8 is a cross-sectional view of the semiconductor device taken along line I-I' of FIG. 7. In the present embodiment, an analysis device configured to measure a fluorescence intensity, concentration, and the like of a specific substance in a sample liquid.

A semiconductor substrate 10 formed of Si or the like is mounted on the center of a support substrate 100. A sensor part 15 configured to detect physical information and chemical information of a sample liquid is provided with the surface of the semiconductor substrate 10. The sensor part 15 includes, for example, fluorescence sensors arranged two-dimensionally. Furthermore, an electrode 101 which is electrically connected to the sensor part 15 is disposed in an area of the support substrate 100 except for the mount area of the semiconductor substrate 10.

On the semiconductor substrate 10, a bank 121 formed of a silicone resin is disposed to surround the sensor part 15. A sample liquid can be stored in the area surrounded by the bank 121. Furthermore, a seal 122 formed of a silicone resin is disposed outside of the inner periphery of the bank 121. The seal 122 is disposed to cover the outside of the inner periphery of the bank 121 and the surface of the support substrate 100.

In such a structure, a sample liquid can be stored in an area (reservoir 130) surrounded by the silicone resin bank 121 and seal 122, and the sample liquid can be inspected by the sensor part 15. In that case, the surface touching the sample liquid is formed of a silicone resin except for the sensor part 15, and thus, the material of the reservoir 130 does not harm the inspection.

FIGS. 9A to 9D are cross-sectional views showing a manufacturing process of the semiconductor device of the seventh embodiment. In this embodiment, for example, a bank structure is formed on a substrate to surround a sensor part formed on a substrate. Note that, in the example of FIGS. 9A to 9D, there are two sensor parts.

Initially, as shown in FIG. 9A, a bank formed of a silicone resin is formed on a semiconductor substrate 10 mounted on a support substrate 100 to surround a sensor part 15. The bank 121 may be manufactured through any method explained in the sections of the first to third embodiments.

Note that the bank 121 may be disposed outside the sensor part 15 or may partly overlap the sensor part 15. Furthermore, the above bank formation may be performed before the semiconductor substrate 10 is mounted on the support substrate 100.

Then, as shown in FIG. 9B, a mask 140 formed of a polyether ether ketone (PEEK) material, a fluorocarbon resin, or the like is formed on the bank 121 to cover the sensor part 15.

Then, as shown in FIG. 9C, a silicone resin is applied to an area uncovered by the mask 140 to form a seal 122 formed of a silicone resin.

Then, as shown in FIG. 9D, the silicone resin of the seal 122 is cured by irradiation of ultraviolet. Then, the mask 140 is removed. Thus, a reservoir 130 side walls of which are formed of a silicone resin is formed on the sensor part 15.

(Note)

Technical significances of the pattern forming method and the semiconductor device explained in the embodiment are as follows.

(1) A pattern forming method comprises: a step of forming a resist pattern 11 on a substrate 10; a step of forming a silicone resin layer 21 such that the resist pattern 11 on the substrate 10 is embedded; a step of pressing a film 31 to a surface of the silicone resin layer 21 to adhere the film 31 thereto; a step of curing the silicone resin layer 21 after adhesion of the film 31; peeling the film 31 from the silicone resin layer 21 before or after the silicone resin layer 21; and removing the resist pattern 11 after peeling the film 31.

(1-1) The step of forming a resist pattern 11 includes forming a convex resist pattern 11 in a reverse pattern of a convex bank structure.

(1-2) The step of adhesion of the film 31 includes pressing a roller 32 to the film 31 to be adhered to the silicone resin layer 21.

(1-3) The pressure used in adhesion of the film 31 is 1 kgf/cm$^2$ or more.

(1-4) The silicone resin layer 21 is ultraviolet-cured and the film 31 is formed of a material passing ultraviolet having a wavelength of 436 nm or less.

(1-5) The step of curing the silicone resin layer 21 includes irradiating ultraviolet to the silicone resin layer 21 through the film 31.

(1-6) The step of curing the silicone resin layer 21 includes irradiating ultraviolet to the silicone resin layer 21 after peeling the film 31.

(1-7) The silicone resin layer 21 is thermal-cured and the step of curing the silicone resin layer 21 includes irradiating infrared to the silicone resin layer 21 or heating the silicone resin layer 21 by a heater.

(1-8) The step of adhesion of the film 31 is performed in a vacuum and a pressure therein is 10 torr or less.

(1-9) After peeling the film 31, a residue of the silicone resin layer 21 on the resist pattern 11 is removed by dry etching or grinding.

(1-10) A developer contains at least one of diisopropylamine, triethylamine, pentane, perfluorotributylamine, perfluorodecalin, xylene, ether, hexane, trichloroethylene, normal heptane, cyclohexane, dimethoxyethane, toluene, ethyl acetate, and ethyl methyl ketone, as a solvent.

(2) A pattern forming method comprises: a step of forming an ultraviolet-cured silicone resin layer 21 on the substrate 10; a step of selectively irradiating ultraviolet on the silicone resin layer 21 to remain the silicone resin layer 21 as a convex; and a step of removing an uncured part of the silicone resin layer 21 by the developer.

(3) A pattern forming method comprises: a step of forming a resist pattern on a substrate 10; a step of forming an ultraviolet-cured silicone resin layer 21 on the substrate 10 with the resist pattern 11 to cover the resist pattern 11; a step of irradiating ultraviolet on the silicone resin layer 21 except for a region of the resist pattern 11 to cure the irradiated part; a step or removing an uncured part of the silicone resin layer 21 by a developer; and a step of removing the resist pattern 11 through the removed part of the silicone resin layer 21.

(3-1) The step of forming the resist pattern 11 includes forming the resist pattern 11 in a reverse pattern of the part to be a convex bank structure.

(4) A pattern forming method comprises: a step of forming a resist pattern 11 to be a channel on a substrate 10; a step of forming an ultraviolet-cured silicone resin layer 21 on the substrate 10 with the resist pattern 11 to cover the resist pattern 11; a step of partly irradiating ultraviolet on the silicone resin layer 21 except for the resist pattern 11 to cure the irradiated part; a step of removing an uncured silicone resin layer 21 by a developer; and a step of removing the resist pattern 11 through the removed part of the silicone resin layer 21.

(4-1) The step of irradiating ultraviolet includes irradiating ultraviolet on the silicone resin layer 21 except for a part to be an opening connected to the channel.

(5) A pattern forming method comprises: a step of forming a resist pattern 11 to be a channel on a substrate 10; a step of forming a protection film 12 to cover the resist pattern 11; a step of forming an ultraviolet-cured silicone resin layer 21 on the substrate 10 with the resist pattern 11 and the protection film 12 to cover the resist pattern 11; a step of partly irradiating ultraviolet on the silicone resin layer 21 except for the resist pattern 11 to cure the irradiated part; a step of removing an uncured silicone resin layer 21 by a developer; a step of selectively etching the protection film 12 using the silicone resin layer 21 as a mask; and a step of removing the resist pattern 11 through the removed parts of the silicone resin layer 21 and the protection film 12.

(5-1) The step of irradiating ultraviolet includes irradiating ultraviolet on the silicone resin layer 21 except for a part to be an opening connected to the channel.

(5-2) The protection film is formed of an oxide film, nitride film, polyparaxylene resin film, or a layered structure thereof.

(6) A pattern forming method comprises: a step of forming a resist pattern 11 as a channel on a substrate 10; a step of forming a silicone resin layer 21 such that the resist pattern 11 on the substrate 10 is embedded; a step of pressing a film 31 to a surface of the first silicone resin layer 21 to adhere to film 31 thereto; a step of curing the first silicone resin layer 21 after adhesion of the film 31; a step of peeling the film 31 from the first silicone resin layer 21 before or after the curing of the film 31; a step of forming an ultraviolet-cured second silicone resin layer 22 on the surface of the resist pattern 11 and the first silicone resin layer 21 after peeling the film 31; a step of partly irradiating ultraviolet on the second silicone resin layer 22 except for the resist pattern 11 to cure the irradiate area; a step of removing an uncured part of the second silicone resin layer 22 by a developer; and a step of removing the resist pattern 11 through the removed part of the second silicone resin layer 22.

(6-1) The step of irradiating ultraviolet includes irradiating ultraviolet on the second silicone resin layer 22 except for a part to be an opening connected to the channel.

(7) A manufacturing method of a semiconductor device, the method includes: a step of forming a first silicone resin layer (bank) 121 on a substrate 10 with a sensor part 15 configured to detect physical information or chemical information of a sample liquid to surround the sensor part 15; a step of forming a mask 40 on the first silicone resin layer 121 to cover an area surrounded by the first silicone resin layer 121; a step of forming a second silicone resin layer (seal) 122 on the first silicone resin layer 121 uncovered by the mask 140 and the substrate 10; a step of curing the second silicone resin layer 122; and a step of removing the mask 140 after curing the second silicone resin layer 122.

(7-1) The sensor part 15 includes fluorescence sensors arranged two-dimensionally.

(7-2) The step of forming the first silicone resin layer 121 includes, after forming the ultraviolet-cured first silicone resin layer 121 on the substrate 10, selectively irradiating ultraviolet on the first silicone resin layer 121 (to the area to be remained as a convex on the substrate 10 to surround the sensor part 15) to cure the irradiated part, and then, removing an uncured part of the first silicone resin layer 121 by a developer.

(7-3) The step of forming the first silicone resin layer 121 includes, after forming the resist pattern 11 on the substrate 10 to cover the sensor part 15, forming a silicone resin layer 121 on the substrate 10 to embed the resist pattern 11, pressing the film 31 to a surface of the silicone resin layer 121 to adhere the film 31 thereto, curing the silicone resin layer 121, peeling the film 31 from the silicone resin layer 121 before or after curing the silicone resin layer 121, and removing the resist pattern 11.

(8) A semiconductor device comprises: a sensor part 15 provided with a substrate 10 and configured to detect physical information or chemical information of a sample liquid; a first silicone resin layer (bank) 121 provided with the substrate 10 to surround the sensor part 15; and a second silicone resin layer (seal) 122 disposed on the substrate 10 and the first silicone resin layer 121 outside the inner periphery of the first silicone resin layer 121.

(Variation)

Note that the present invention is not limited to the above embodiments.

The embodiments show a bank surrounding a sensor part; however, the embodiments may be applied to manufacturing of a semiconductor device with silicone resin convex pattern.

The embodiments use ultraviolet-cured silicone resin; however, a silicone resin selectively cured by some energy can be used instead.

A resist as a frame is not limited to a photoresist, and any material which is easily patterned and selectively removed with respect to a silicone resin can be used.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A pattern forming method, comprising:
  forming a resist pattern on a substrate;
  forming a silicone resin layer which is ultraviolet-cured on the substrate with the resist pattern formed thereon;
  selectively irradiating ultraviolet on the silicone resin layer, the ultraviolet not being irradiated at least on a region corresponding to the resist pattern, to cure the irradiated area;
  removing an uncured part of the silicone resin layer by a developer; and
  removing the resist pattern through a part where the silicon resin layer is removed.

2. The method of claim 1, wherein the resist pattern is formed as a reverse pattern of a part where a convex bank structure is to be formed.

3. The method of claim 2, wherein the resist pattern is formed as pattern for a channel on the substrate, and the ultraviolet is not irradiated on a part corresponding to an opening connected to the channel.

4. The method of claim 2, wherein, after the forming of the resist pattern and before the forming of the silicone resin layer, a protection film is formed to cover the resist pattern, and, after the removing of the uncured part of the silicone resin layer by the developer and before the removing of the resist pattern, the protection film is selectively etched using the silicon resin layer as a mask.

5. The method of claim 1, wherein the developer includes at least one of diisopropylamine, triethylamine, pentane, perfluorotributylamine, perfluorodecalin, xylene, ether, hexane, trichloroethylene, normal heptane, cyclohexane, dimethoxyethane, toluene, ethyl acetate, and ethyl methyl ketone, as a solvent.

* * * * *